(12) United States Patent
Peglion et al.

(10) Patent No.: US 8,101,747 B2
(45) Date of Patent: Jan. 24, 2012

(54) PROCESS FOR THE SYNTHESIS OF IVABRADINE AND ADDITION SALTS THEREOF WITH A PHARMACEUTICALLY ACCEPTABLE ACID

(75) Inventors: Jean-Louis Peglion, Le Vesinet (FR); Aimee Dessinges, Rueil Malmaison (FR); Bernard Serkiz, Servon Brie Comte Robert (FR)

(73) Assignee: Les Laboratoires Servier, Suresnes Cedex (FR)

( * ) Notice: Subject to any disclaimer, the term of this patent is extended or adjusted under 35 U.S.C. 154(b) by 171 days.

(21) Appl. No.: 12/798,042

(22) Filed: Mar. 29, 2010

(65) Prior Publication Data
US 2010/0249397 A1 Sep. 30, 2010

(30) Foreign Application Priority Data
Mar. 31, 2009 (FR) ...................... 09 01555

(51) Int. Cl.
*C07D 223/16* (2006.01)
(52) U.S. Cl. ..................................................... 540/523
(58) Field of Classification Search .................. 540/523
See application file for complete search history.

(56) References Cited

FOREIGN PATENT DOCUMENTS
EP 0534859 3/1993
GB 1140049 1/1969
WO WO 2005/110993 11/2005

OTHER PUBLICATIONS

French Preliminary Search Report for FR0901555 of Aug. 27, 2009.
Rousselet, et al., Copper(I)-induced addition of amines to unactivatied nitriles: The first general one-step synthesis of alkyl amidines: Tetrahedron Letters, vol. 34, No. 40, p. 6395-6398, Oct. 1, 1993.

*Primary Examiner* — Bruck Kifle
(74) *Attorney, Agent, or Firm* — Hueschen and Sage

(57) ABSTRACT

Process for the synthesis of ivabradine of formula (I):

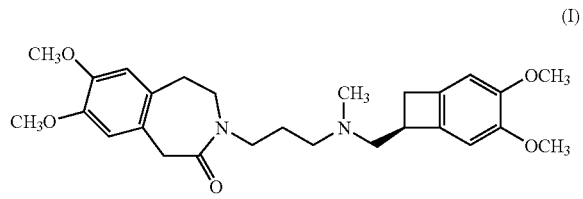

(I)

and addition salts thereof with a pharmaceutically acceptable acid.

12 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

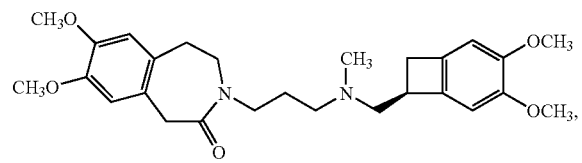

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid, and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the synthesis of ivabradine hydrochloride starting from the compound of formula (II):

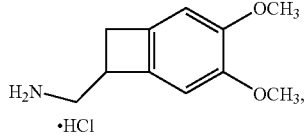

which is converted into the compound of formula (III):

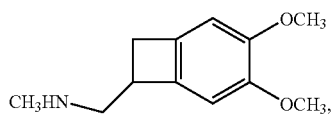

which is resolved to yield the compound of formula (IV):

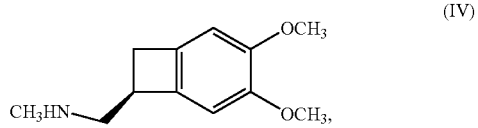

which is reacted with the compound of formula (V):

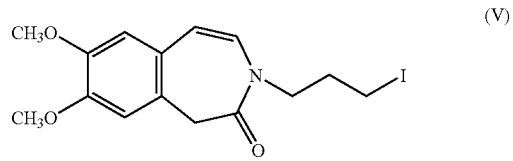

to yield the compound of formula (VI):

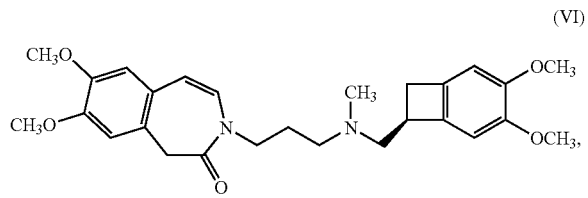

the catalytic hydrogenation of which yields ivabradine, which is then converted into its hydrochloride.

The disadvantage of that synthesis route is that it results in ivabradine in a yield of the order of only 0.6%.

In view of the pharmaceutical value of this compound, it has been important to be able to obtain it by an effective synthesis process resulting in ivabradine in a good yield.

The present invention relates to a process for the synthesis of the compound of formula (VII), in racemic or optically active form:

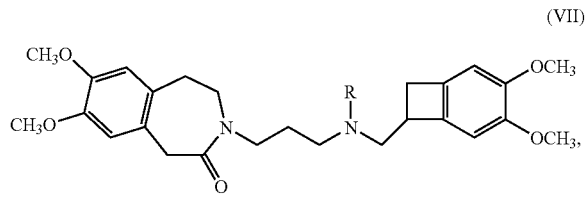

wherein R represents a hydrogen atom or a methyl group, characterised in that the compound of formula (VIII):

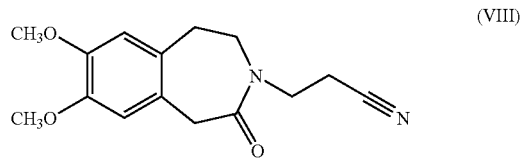

is reacted with the compound of formula (IX), in racemic or optically active form, in the form of the free base or a salt:

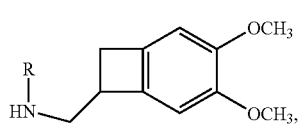

(IX)

wherein R is as defined hereinbefore,
in the presence of a salt of a transition metal or of a lanthanide, in a solvent,
to yield the compound of formula (X), in racemic or optically active form:

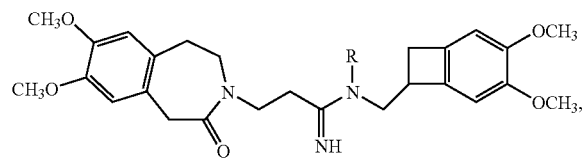

(X)

which is converted into the compound of formula (VII) by the action of a hydride donor agent.

In a preferred embodiment of the invention, the compound of formula (IX) is in optically active form, more especially of configuration (S).

In the case where R represents a hydrogen atom, the product of the reaction of the compound of formula (X) with the hydride donor agent is then the compound of formula (XI), a particular case of the compounds of formula (VII):

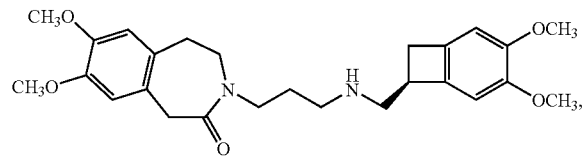

(XI)

which may be N-methylated to yield ivabradine of formula (I):

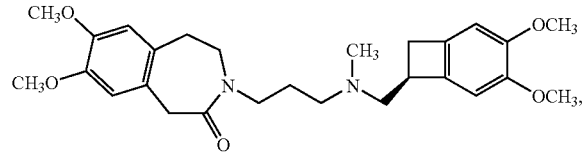

(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

In the case where R represents a methyl group, the product of the reaction of the compound of formula (X) with the hydride donor agent is then ivabradine of formula (I), a particular case of the compounds of formula (VII):

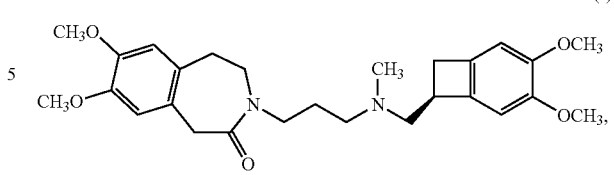

(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

In another preferred embodiment of the invention, the compound of formula (IX) is in racemic form.

In the case where R represents a hydrogen atom, the product of the reaction of the compound of formula (X) with the hydride donor agent is then the racemic compound of formula (XII), a particular case of the compounds of formula (VII):

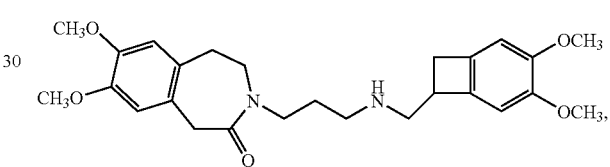

(XII)

which may be N-methylated to yield the racemic compound of formula (XIII):

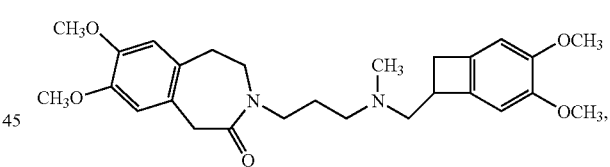

(XIII)

the optical resolution of which yields ivabradine of formula (I):

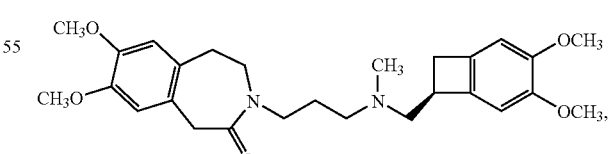

(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

In the case where R represents a methyl group, the product of the reaction of the compound of formula (X) with the hydride donor agent is then the racemic compound of formula (XIII), a particular case of the compounds of formula (VII):

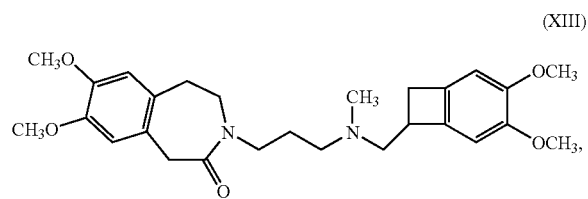

(XIII)

the optical resolution of which yields ivabradine of formula (I):

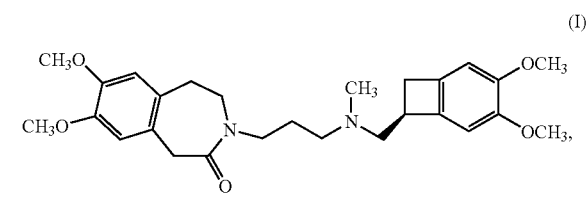

(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Among the salts of transition metals or of lanthanides that may be used to carry out the reaction between the compound of formula (VIII) and the compound of formula (IX), there may be mentioned, without implying any limitation, copper (I) chloride, copper(I) bromide, copper(I) iodide, yttrium(III) trifluoromethanesulphonate, lanthanum(III) trifluoromethanesulphonate, praseodymium(III) trifluoromethanesulphonate, neodymium(III) trifluoromethanesulphonate, samarium(III) trifluoromethanesulphonate, europium(III) trifluoromethanesulphonate, gadolinium(III) trifluoromethanesulphonate, terbium(III) trifluoromethanesulphonate, dysprosium(III) trifluoromethanesulphonate, holmium (III) trifluoromethanesulphonate, erbium(III) trifluoromethanesulphonate and lutetium(III) trifluoromethanesulphonate.

Preference is given to the transition metal salt used for carrying out the reaction between the compound of formula (VIII) and the compound of formula (IX) being copper(I) chloride.

Among the solvents that may be used for carrying out the reaction between the compound of formula (VIII) and the compound of formula (IX) there may be mentioned, without implying any limitation:
- alcoholic solvents, especially methanol, ethanol and isopropanol;
- dimethyl sulphoxide (DMSO);
- N,N-dimethylformamide (DMF);
- N-methylpyrrolidone (NMP).

Preference is given to the solvent used for carrying out the reaction between the compound of formula (VIII) and the compound of formula (IX) being methanol.

Among the hydride donor agents that may be used for carrying out the conversion of the compound of formula (X) into the compound of formula (VII) there may be mentioned, without implying any limitation, sodium tetraborohydride, sodium cyanoborohydride and also the complexes borane-morpholine and borane-dimethylamine.

Among the solvents that may be used for carrying out the conversion of the compound of formula (X) into the compound of formula (VII) there may be mentioned, without implying any limitation:
- alcoholic solvents, especially methanol, ethanol and isopropanol;
- N,N-dimethylformamide (DMF);
- N-methylpyrrolidone (NMP).

The compounds of formulae (VIII) and (X) are new products which are useful as synthesis intermediates in the chemical or pharmaceutical industry, especially in the synthesis of ivabradine, addition salts thereof with a pharmaceutically acceptable acid and hydrates thereof, and as such they form an integral part of the present invention.

The Examples hereinbelow illustrate the invention.

LIST OF ABBREVIATIONS USED

DMF: N,N-dimethylformamide
IR: infra-red
The melting points (m.p.) were measured using a micro Köfler (MK) apparatus.

EXAMPLE 1

3-(7,8-Dimethoxy-2-oxo-1,2,4,5-tetrahydro-3H-3-benzazepin-3-yl)-propanenitrile 2 g (9 mmol) of 7,8-dimethoxy-1,3,4,5-tetrahydro-2H-3-benzazepin-2-one are dissolved in 30 mL of DMF. To the resulting solution there are added, at 25° C., 432 mg (10.8 mmol, 1.2 equivalents) of sodium hydride as a 60% suspension in oil. Stirring is carried out for 30 minutes at ambient temperature and there is then added a solution of 0.9 mL (10.8 mmol, 1.2 equivalents) of 3-bromopropionitrile in 10 mL of DMF. Heating at 50° C. is then carried out for 24 hours, and then the solvent is evaporated off. The residue is taken up in dichloromethane, washed with water, dried over MgSO$_4$, filtered and evaporated to dryness. There are obtained 4.1 g of a residue, which is purified by flash chromatography on 300 g of silica (eluant=dichloromethane/ethanol:95/5). There are obtained 630 mg of the title product in the form of an oil, and 1 g of unreacted 7,8-dimethoxy-1,3,4,5-tetrahydro-2H-3-benzazepin-2-one is recovered (white solid, m.p.=196-198° C.).

Yield=26% IR (pure): ν=2247, 1648, 1609, 1518, 1246, 1220, 1104 cm$^{-1}$.

EXAMPLE 2

3-[3-({[(7S)-3,4-Dimethoxybicyclo[4.2.0]octa-1,3,5-trien-7-yl]methyl}-amino)propyl]-7,8-dimethoxy-1,3,4,5-tetrahydro-2H-3-benzazepin-2-one Step 1: N-{[(7S)-3,4-dimethoxybicyclo[4.2.0]octa-1,3,5-trien-7-yl]methyl}-3-(7,8-dimethoxy-2-oxo-1,2,4,5-tetrahydro-3H-3-benzazepin-3-yl)propanimidamide Under nitrogen, 630 mg (3.27 mmol, 1.5 equivalents) of 1-[(7S)-3,4-dimethoxybicyclo-[4.2.0]octa-1,3,5-trien-7-yl]

methanamine hydrochloride are dissolved in 10 mL of methanol. To the resulting solution there are added 0.46 mL (3.27 mmol, 1.5 equivalents) of triethylamine and 260 mg (2.62 mmol) of copper(I) chloride (purity: 90%). Then 600 mg (2.18 mmol) of 3-(7,8-dimethoxy-2-oxo-1,2,4,5-tetrahydro-3H-3-benzazepin-3-yl)propanenitrile dissolved in 10 mL of methanol are added dropwise. Heating at reflux is carried out for 12 hours, then cooling to ambient temperature, and 5 mL of 35% aqueous sodium hydroxide solution and 30 mL of dichloromethane are added. The organic phase is extracted, dried over MgSO$_4$, filtered and then evaporated to dryness. There are obtained 1.08 g of a brown oil containing 47% expected product. This oil is used without purification in the step that follows.

Step 2: 3-[3-({[(7S)-3,4-Dimethoxybicyclo[4.2.0]octa-1,3,5-trien-7-yl]methyl}amino)propyl]-7,8-dimethoxy-1,3,4,5-tetrahydro-2H-3-benzazepin-2-one 1 g of the product obtained in Step 1 (containing 47% amidine) is dissolved in 15 mL of methanol; the resulting solution is then cooled to 0° C. and 100 mg (2.61 mmol, 1.2 equivalents) of sodium tetraborohydride are added. Stirring is carried out overnight at ambient temperature, and then 5.3 mL of 20% aqueous sodium hydroxide solution and 20 mL of dichloromethane are added. Vigorous stirring is carried out for 15 minutes. The organic phase is then extracted, washed with water, dried over MgSO$_4$, filtered and then evaporated to dryness. There is obtained 1 g of an oil which is purified by flash chromatography on 100 g of silica (eluant=dichloromethane/ethanol/NH$_4$OH: 90/10/1) to yield 300 mg of expected product in the form of an oil.

Yield=30% (over 2 steps) IR (pure): v=3302, 1649 cm$^{-1}$.

EXAMPLE 3

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one Step 1: 3-[3-({[(7S)-3,4-Dimethoxybicyclo[4.2.0]octa-1,3,5-trien-7-yl]methyl}amino)propyl]-7,8-dimethoxy-1,3,4,5-tetrahydro-2H-3-benzazepin-2-one hydrochloride 300 mg (0.65 mmol) of the amine obtained in Example 2, Step 2, are dissolved in 10 mL of acetonitrile. To the resulting solution there is added 0.65 mL (1.3 mmol, 2 equivalents) of 2M hydrochloric acid solution in diethyl ether. Stirring is carried out at 25° C. for 15 minutes, and then evaporation to dryness. The product is crystallised from 20 mL of acetone. The solid is filtered off and dried. 230 mg of white crystals are obtained.

Yield=71% m.p.=204-206° C.

Step 2: 3-{3-[{[(7S)-3,4-dimethoxybicyclo[4.2.0]octa-1,3,5-trien-7-yl]methyl}(methyl)amino]propyl}-7,8-dimethoxy-1,3,4,5-tetrahydro-2H-3-benzazepin-2-one 180 mg (0.36 mmol) of hydrochloride obtained in Step 1 are dissolved in a mixture of 10 mL of methanol and 5 mL of dichloromethane. To the resulting solution there are added 0.04 mL (0.54 mmol, 1.5 equivalents) of formaldehyde (37% in water) and a grain of bromocresol green. 1N aqueous hydrochloric acid solution is added until the pH is 4 (yellow-coloured solution) and then stirring is carried out at 25° C. for 30 minutes. There are then added 23 mg (0.36 mmol) of sodium cyanoborohydride, stirring is carried out at 25° C. for 12 hours whilst maintaining the pH at 4, and then evaporation to dryness is carried out. There are obtained 250 mg of an oil which is purified by flash chromatography on 100 g of silica (eluant=dichloromethane/ethanol/NH$_4$OH: 90/10/1) to yield 100 mg of the title product in the form of a colourless oil which crystallises at ambient temperature.

Yield=58% m.p.=98-100° C.

EXAMPLE 4

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one hydrochloride The hydrochloride of the product obtained in Example 3, Step 2, is prepared by following the procedure described in patent specification EP 0 534 859 (Example 2, Step E).

EXAMPLE 5

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one Step 1: N-{[(7S)-3,4-Dimethoxybicyclo[4.2.0]octa-1,3,5-trien-7-yl]methyl}-3-(7,8-dimethoxy-2-oxo-1,2,4,5-tetrahydro-3H-3-benzazepin-3-yl)-N-methylpropanimidamide Under nitrogen, 691 mg (2.83 mmol, 1.5 equivalents) of 1-[(7S)-3,4-dimethoxybicyclo-[4.2.0]octa-1,3,5-trien-7-yl]-N-methylmethanamine hydrochloride are dissolved in 10 mL of methanol. To the resulting solution there are added 0.4 ml (2.83 mmol, 1.5 equivalents) of triethylamine and 224 mg (2.26 mmol) of copper(I) chloride (purity: 90%). Then 520 mg (1.89 mmol) of 3-(7,8-dimethoxy-2-oxo-1,2,4,5-tetrahydro-3H-3-benzazepin-3-yl)propanenitrile dissolved in 10 mL of methanol are added dropwise. Heating at reflux is carried out for 24 hours, then cooling to ambient temperature, and 5 mL of 35% aqueous sodium hydroxide solution and 30 mL of dichloromethane are added. The organic phase is extracted, dried over MgSO$_4$, filtered and then evaporated to dryness. There are obtained 1.08 g of a brown oil containing 46% expected product. This oil is used without purification in the step that follows.

Step 2: 3-{3-[{[(7S)-3,4-Dimethoxybicyclo[4.2.0]octa-1,3,5-trien-7-yl]methyl}(methyl)amino]propyl}-7,8-dimethoxy-1,3,4,5-tetrahydro-2H-3-benzazepin-2-one 1 g of the product obtained in Step 1 (containing 46% amidine) is dissolved in 15 mL of methanol and then 86 mg (2.26 mmol, 1.2 equivalents) of sodium tetraborohydride are added at ambient temperature. Stirring is carried out overnight at ambient temperature, and then 5 mL of 20% aqueous sodium hydroxide solution and 20 mL of dichloromethane are added. Vigorous stirring is carried out for 15 minutes. The organic phase is then extracted, washed with water, dried over MgSO$_4$, filtered and then evaporated to dryness. There is obtained 1 g of an oil which is purified by flash chromatography on 100 g of silica (eluant=dichloromethane/ethanol/NH$_4$OH: 90/10/1) to yield 210 mg of the title product in the form of an oil.

Yield=24% (over 2 steps) IR (pure): v=1633, 831-672 cm$^{-1}$.

EXAMPLE 6

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one hydrochloride The hydrochloride of the product obtained in Example 5, Step 2, is prepared by following the procedure described in patent specification EP 0 534 859 (Example 2, Step E).

EXAMPLE 7

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one hydrochloride Starting from racemic (3,4-dimethoxybicyclo[4.2.0]octa-1,3,5-trien-7-yl)methanamine, and following the protocol described by the sequence of Examples 2 and 3, 3-{3-[[(3,4-dimethoxybicyclo[4.2.0]octa-1,3,5-trien-7-yl)methyl](methyl)amino]propyl}-7,8-dimethoxy-1,3,4,5-tetrahydro-2H-3-benzazepin-2-one is obtained.

2.1 g of this racemic compound are then separated on a 60 cm×60 mm column packed with 2.1 kg of Chiralpak® AD phase (particle size 20 μm). The eluant used is a mixture of ethanol/acetonitrile/diethylamine (10/90/0.1 by volume) at a flow rate of 50 mL/min. The associated ultra-violet detector is used at a wavelength of 280 nm.

There are obtained 0.95 g of the enantiomer of configuration (R) in the form of a white meringue and then 0.95 g of the enantiomer of configuration (S), also in the form of a white meringue.

The hydrochloride of the enantiomer of configuration (S) is then obtained by following the procedure described in patent specification EP 0 534 859 (Example 2, Step E).

EXAMPLE 8

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one hydrochloride Starting from racemic (3,4-dimethoxybicyclo[4.2.0]octa-1,3,5-trien-7-yl)-N-methyl-methanamine, and by following the protocol described in Example 5, there is obtained 3-{3-[[(3,4-dimethoxybicyclo[4.2.0]octa-1,3,5-trien-7-yl)methyl](methyl)amino]propyl}-7,8-dimethoxy-1,3,4,5-tetrahydro-2H-3-benzazepin-2-one.

2.1 g of this racemic compound are then separated on a 60 cm×60 mm column packed with 2.1 kg of Chiralpak® AD phase (particle size 20 μm). The eluant used is a mixture of ethanol/acetonitrile/diethylamine (10/90/0.1 by volume) at a flow rate of 50 mL/min. The associated ultra-violet detector is used at a wavelength of 280 nm.

There are obtained 0.95 g of the enantiomer of configuration (R) in the form of a white meringue and then 0.95 g of the enantiomer of configuration (S), also in the form of a white meringue.

The hydrochloride of the enantiomer of configuration (S) is then obtained by following the procedure described in patent specification EP 0 534 859 (Example 2, Step E).

The invention claimed is:

1. A process for the synthesis of the compound of formula (VII), in racemic or optically active form:

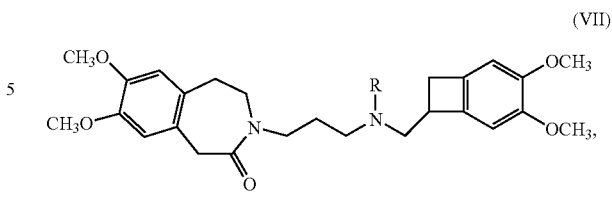

(VII)

wherein R represents a hydrogen atom or a methyl group, wherein a compound of formula (VIII):

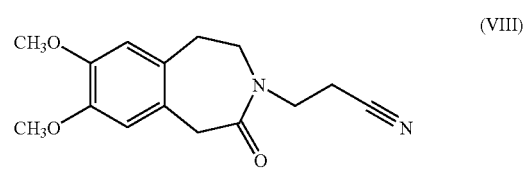

(VIII)

is reacted with a compound of formula (IX), in racemic or optically active form, in the form of the free base or a salt:

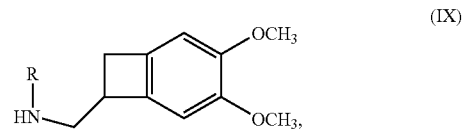

(IX)

wherein R is as defined hereinbefore, in the presence of a salt of a transition metal or of a lanthanide, in a solvent, to yield a compound of formula (X), in racemic or optically active form:

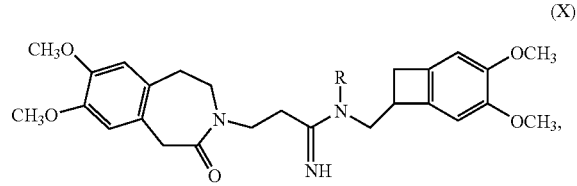

(X)

which is converted into a compound of formula (VII) by the action of a hydride donor agent.

2. The process of claim 1, wherein the compound of formula (IX) is of configuration (S).

3. The process of claim 2, wherein R represents a hydrogen atom, and wherein the product of the reaction of the compound of formula (X) with the hydride donor agent is a compound of formula (XI):

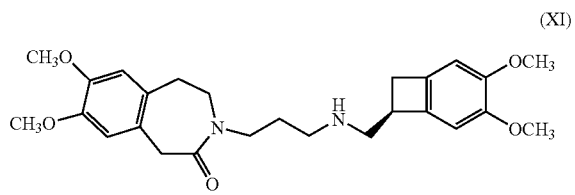

which may be N-methylated to yield ivabradine of formula (I):

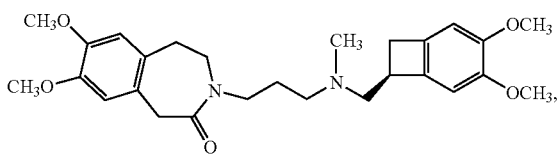

which may optionally be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into a hydrate thereof.

4. The process of claim 2, wherein R represents a methyl group, and wherein the product of the reaction of the compound of formula (X) with the hydride donor agent is ivabradine of formula (I):

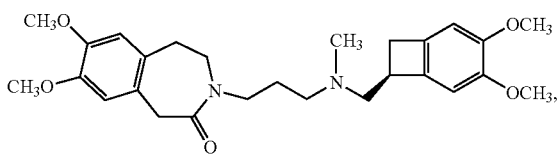

which may optionally be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into a hydrate thereof.

5. The process of claim 1, wherein the compound of formula (IX) is in racemic form.

6. The process of claim 5, wherein R represents a hydrogen atom, and wherein the product of the reaction of the compound of formula (X) with the hydride donor agent is a racemic compound of formula (XII):

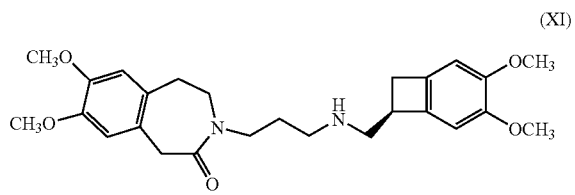

which may be N-methylated to yield a racemic compound of formula (XIII):

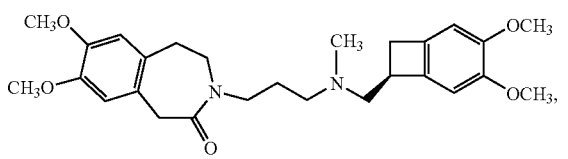

the optical resolution of which yields ivabradine of formula (I):

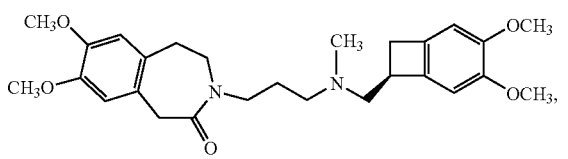

which may optionally be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into a hydrate thereof.

7. The process of claim 5, wherein R represents a methyl group, and wherein the product of the reaction of the compound of formula (X) with the hydride donor agent is the racemic compound of formula (XIII):

the optical resolution of which yields ivabradine of formula (I):

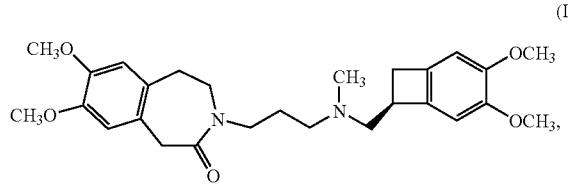

(I)

which may optionally be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into a hydrate thereof.

8. The process of claim 1, wherein the salt of a transition metal or of a lanthanide used to carry out the reaction between the compound of formula (VIII) and the compound of formula (IX) is selected from copper(I) chloride, copper(I) bromide, copper(I) iodide, yttrium(III) trifluoromethanesulphonate, lanthanum(III) trifluoromethanesulphonate, praseodymium(III) trifluoromethanesulphonate, neodymium(III) trifluoromethanesulphonate, samarium(III) trifluoromethanesulphonate, europium(III) trifluoromethanesulphonate, gadolinium(III) trifluoromethanesulphonate, terbium(III) trifluoromethanesulphonate, dysprosium(III) trifluoromethanesulphonate, holmium(III) trifluoromethanesulphonate, erbium(III) trifluoromethanesulphonate and lutetium(III) trifluoromethanesulphonate.

9. The process of claim 1, wherein the solvent used to carry out the reaction between the compound of formula (VIII) and the compound of formula (IX) is selected from alcoholic solvents, dimethyl sulphoxide, N,N-dimethylformamide and N-methylpyrrolidone.

10. The process of claim 1, wherein the hydride donor agent used to carry out the conversion of the compound of formula (X) to the compound of formula (VII) is selected from sodium tetraborohydride, sodium cyanoborohydride, the complex borane-morpholine and the complex borane-dimethylamine.

11. A compound of formula (VIII):

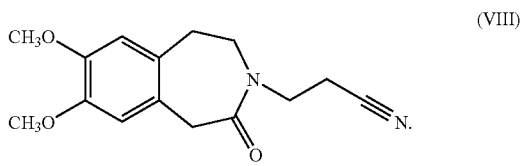

(VIII)

12. A compound of formula (X), in racemic or optically active form:

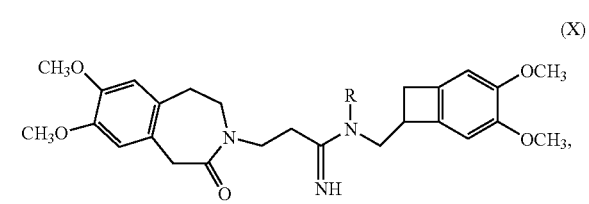

(X)

wherein R represents a hydrogen atom or a methyl group.

* * * * *